US007453015B2

(12) United States Patent
Van Kruchten et al.

(10) Patent No.: US 7,453,015 B2
(45) Date of Patent: Nov. 18, 2008

(54) PROCESS FOR THE PREPARATION OF ALKYLENE GLYCOLS

(75) Inventors: Eugene Marie Godfried Andre Van Kruchten, Amsterdam (NL); Hendrik Stichter, Amsterdam (NL); Johannes Theodorus Gertruda Wijenberg, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/461,334

(22) Filed: Jul. 31, 2006

(65) Prior Publication Data

US 2007/0191648 A1 Aug. 16, 2007

(30) Foreign Application Priority Data

Aug. 2, 2005 (EP) ................... 05254834

(51) Int. Cl.
*C07C 29/00* (2006.01)
(52) U.S. Cl. .................................... 568/867
(58) Field of Classification Search .................. 568/867
See application file for complete search history.

(56) References Cited

U.S. PATENT DOCUMENTS

| | | | | |
|---|---|---|---|---|
| 4,160,116 A | 7/1979 | Mieno et al. | ............. | 568/867 |
| 4,283,580 A | 8/1981 | Odanaka et al. | ............. | 568/858 |
| 4,307,256 A | 12/1981 | Cipriani et al. | ............. | 568/867 |
| 4,314,945 A | 2/1982 | McMullen et al. | ......... | 260/340.2 |
| 4,786,741 A | 11/1988 | Sachs | ............. | 549/230 |
| 4,982,021 A | 1/1991 | Best et al. | ............. | 568/867 |
| 5,138,073 A | 8/1992 | Harvey | ............. | 549/230 |
| 5,488,184 A | 1/1996 | Reman et al. | ............. | 568/867 |
| 6,080,897 A | 6/2000 | Kawabe | ............. | 568/858 |
| 6,124,508 A | 9/2000 | Van Kruchten | ............. | 568/867 |
| 6,153,801 A | 11/2000 | Van Kruchten | ............. | 568/867 |
| 2005/0014980 A1 | 1/2005 | Van Hal et al. | ............. | 568/867 |
| 2007/0179303 A1 | 8/2007 | Van Kruchten et al. | ...... | 549/228 |

FOREIGN PATENT DOCUMENTS

| | | |
|---|---|---|
| EP | 156449 | 3/1985 |
| EP | 1034158 | 9/2000 |
| JP | 56-092228 | 7/1981 |
| JP | 56092228 | 7/1981 |
| JP | 56-128778 | 10/1981 |
| JP | 57-106631 | 7/1982 |
| JP | 59-013741 | 1/1984 |
| JP | 2001/151711 | 6/2001 |
| JP | 2001/151713 | 6/2001 |

OTHER PUBLICATIONS

Notice of Allowance for U.S. Appl. No. 11/461,325 dated Apr. 21, 2008.
Kasuga, K. et al. "The fixation of carbon dioxide with 1,2-epoxypropane catalyzed by alkali-metal halide in the presence of a crown ether", Inorganica Chimica ACTA, vol. 257, 1997, pp. 277-278.
Aldrich: Handbook of Fine Chemicals and Laboratory Equipment. 15-Crown 5 entry and Material Data Safety Sheet. Aldrich Catalogue. Handbook of Fine Chemicals, 2006.
Rokicki et al, Cyclic Carbonates Obtained by Reactions of Metal Carbonates with Epihalohydrins >>, Bulletin of the Chemical Society, Japan, Tokyo, vol. 57, No. 6, 1984, pp. 1662-1666.
Abbas-Alli G. Shaikh and Swaminathan Sivaram, "Organic Cabonates", Chem. Rev., 1996, 96, pp. 951-976.

*Primary Examiner*—Sikarl A Witherspoon

(57) ABSTRACT

A process for the conversion of an alkylene oxide to the corresponding alkylene glycol in the presence of a catalytic composition, carbon dioxide and water, wherein the catalytic composition comprises a halide, a metalate and optionally a macrocyclic chelating compound.

21 Claims, No Drawings

PROCESS FOR THE PREPARATION OF ALKYLENE GLYCOLS

This application claims the benefit of EPC 05254834.4.

FIELD OF THE INVENTION

The invention relates to a process for the catalytic conversion of alkylene oxides to alkylene glycols.

BACKGROUND OF THE INVENTION

Alkylene glycols, in particular monoalkylene glycols, are of established commercial interest. For example, monoalkylene glycols are used in anti-freeze compositions, as solvents and as base materials in the production of polyalkylene terephthalates e.g. for fibres or bottles.

The production of alkylene glycols by liquid phase hydrolysis of alkylene oxide is known. The hydrolysis is generally performed by adding a large excess of water, e.g. 20 to 25 moles of water per mole of alkylene oxide. The reaction is considered to be a nucleophilic substitution reaction, whereby opening of the alkylene oxide ring occurs, water acting as the nucleophile. Because the primarily formed monoalkylene glycol also acts as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Considerable efforts have been made to find an alternative means for increasing the reaction selectivity without having to use a large excess of water. The hydrolysis of alkylene oxides to alkylene glycols can be performed with a smaller excess of water in a catalytic system. Therefore, these efforts have usually focused on the selection of more active hydrolysis catalysts and various catalysts have been disclosed in the literature.

Catalytic processes, promoting a higher selectivity to monoalkylene glycol product at reduced water levels are known (e.g. EP-A-0,156,449, U.S. Pat. Nos. 4,982,021, 5,488,184, 6,153,801 and 6,124,508). Such catalysts often comprise a strongly basic (anionic) exchange resin, often with quaternary ammonium or quaternary phosphonium electropositive complexing sites, coordinated with one or more anions (e.g. metalate, halogen, bicarbonate, bisulfite or carboxylate).

Further examples of catalytic processes known for the reaction of alkylene oxides to alkylene glycols are given in JP 2001151713 and JP 2001151711, wherein a catalytic composition comprising a halide ion and a bicarbonate ion is used to convert an alkylene oxide to the corresponding alkylene glycol in the presence of carbon dioxide and water.

JP-A-56,092,228 is directed to the use of molybdenum and/or tungsten as a catalyst for the conversion of alkylene oxide to alkylene glycol, again in the presence of carbon dioxide and water.

U.S. Pat. No. 4,307,256 describes the reaction of alkylene oxides with water and carbon dioxide in the presence of a tertiary amine catalyst for the production of alkylene glycols.

In U.S. Pat. No. 4,160,116 a similar system is described, wherein the catalyst used is a quaternary phosphonium salt.

EP-A-1,034,158 is directed to the use of a catalytic composition comprising a macrocyclic chelating compound complexed with an ionic compound selected from the group comprising halogenides, carboxylates, hydrogen carbonates, hydrogen sulphites, hydrogen phosphates and metalates, for the hydrolysis of alkylene oxides to alkylene glycols.

In addition, processes for the production of alkylene glycols from alkylene oxides, comprising a two-step process, have been described in the art. Such processes involve the reaction of alkylene oxides with carbon dioxide in the presence of a catalyst, followed by subsequent thermal or catalytic hydrolysis of the resultant alkylene carbonate. Examples of such two-step processes include those described in JP-A-57,106,631 and JP-A-59,013,741.

Catalysts suitable for the hydrolysis of alkylene carbonates are described in U.S. Pat. No. 4,283,580, which is directed to the use of molybdenum or tungsten in metal or compound form as catalysts in the production of substituted or unsubstituted ethylene glycols by the reaction of substituted or unsubstituted ethylene carbonates with water.

Although progress has been made in the hydrolysis of alkylene oxide to alkylene glycol, the need for new processes with increased levels of conversion using highly active and selective catalyst compositions still remains.

SUMMARY OF THE INVENTION

The present invention provides a process for the conversion of an alkylene oxide to the corresponding alkylene glycol in the presence of a catalytic composition, carbon dioxide and water, wherein the catalytic composition comprises a halide, a metalate, and optionally a macrocyclic chelating compound.

DETAILED DESCRIPTION OF THE INVENTION

We have surprisingly found that alkylene glycols may be obtained with a improved activity and/or selectivity by reaction of the corresponding alkylene oxide in the presence of water and carbon dioxide with a catalytic composition comprising a metalate, a halide and, optionally, a macrocyclic chelating compound.

The process of the present invention proceeds with increased activity and selectivity in comparison to the direct hydrolysis of alkylene oxides to alkylene glycols as described in the prior art. Further, this process also proceeds with increased selectivity to the mono-alkylene glycol over both the alkylene carbonate and higher alkylene glycols, compared to processes described in the prior art for the conversion of alkylene oxides to alkylene glycols via the corresponding alkylene carbonate.

The alkylene oxides used as starting material in the process of the invention have their conventional definition, i.e. they are compounds having a vicinal oxide (epoxy) group in their molecules.

Particularly suitable are alkylene oxides of the general formula (I),

wherein $R^1$ to $R^4$ independently represent a hydrogen atom or an optionally substituted, alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$-$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane and 2,3-epoxybutane. In the present invention the most preferred alkylene oxide is ethylene oxide.

The preparation of alkylene oxides is well known to the skilled person. In the case of ethylene oxide, it may be prepared by the well known direct oxidation of ethylene, i.e. by air or oxygen oxidation, utilizing silver-based catalysts and often also organic moderators, e.g. organic halides (see for example Kirk Othmer's Encyclopedia of Chemical Technology, $4^{th}$ edition, Vol. 9, pages 923-940).

As used herein, the term 'metalate' is defined as a metal oxide anion in which the metal is polyvalent, having a positive functional oxidation state of at least +3, and may, for example, be a transition metal. In the present invention, the metalate is suitably selected from metal oxide anions comprising group 5 and 6 metals (according to IUPAC Nomenclature of Inorganic Chemistry, Recommendations 1990. Blackwell Scientific Publications, 1990. Edited by G J Leigh). Preferably, the metalate is selected from the group of tungstates, vanadates and molybdates. Most preferably the metalate is a molybdate.

Typical examples of such metalate anions include anions conventionally characterized by the formulae $[MoO_4]^{2-}$, $[VO_3]^-$, $[V_2O_7H]^{3-}$, $[V_2O_7]^{4-}$ and $[WO_4]^{2-}$. It is recognized that the chemistry of these metalate anions is complex and the exact chemical formula under the conditions of the process of the present invention may prove to be different, but the above is the commonly accepted characterization.

The amount of metalate used in the process of the present invention is suitably in the range of from 0.0001 to 0.5 mol/mol alkylene oxide. Preferably, the metalate is present in an amount in the range of from 0.001 to 0.1 mol/mol alkylene oxide.

The term halide refers to a compound comprising an anion of one of the elements of group 17 of the periodic table (according to IUPAC Nomenclature of Inorganic Chemistry, Recommendations 1990. Blackwell Scientific Publications, 1990. Edited by G J Leigh). Preferably, the halide is selected from the group of chlorides, bromides and iodides. Most preferably, the halide is an iodide.

Suitable halides include quaternary phosphonium halides, quaternary ammonium halides and alkali metal halides.

The amount of halide used in the process of the present invention is suitably in the range of from 0.0001 to 0.5 mol/mol alkylene oxide. Preferably, the halide is present in an amount in the range of from 0.001 to 0.1 mol/mol alkylene oxide.

Macrocyclic chelating compounds are known—see for example J. March in Advanced Organic Chemistry; Reactions, Mechanisms and Structures, $4^{th}$ Edition 1992, pp 82-87 and 363-364. They have the property of forming complexes with positive ions (cations), although they can also complex neutral molecules. They have a regular organic ring structure containing a plurality of hetero-atoms such as oxygen, nitrogen or sulphur. They can be monocyclic, bicyclic or cycles of a higher order. The bonding of cations in these complexes is the result of ion-dipole attractions between the heteroatoms and the positive ions. Thus, the number of the heteroatoms in the molecule determines the binding strength and the size and shape of the cavity determines the ions (or neutral molecules) that can be bound. The macrocycle is called the host and the ion is the guest. Owing to their shape and size, the ability of the host molecules to bind guests is often very specific, enabling the host to pull just one cation or molecule out of a mixture.

It is envisaged that any macrocyclic chelating compound may be utilized in the process of the present invention.

The best-known macrocyclic chelating compounds are those wherein all or most of the heteroatoms are oxygen, in particular the crown ethers wherein the ring structure is two-dimensional (monocyclic) and the cryptands wherein the ring structure is three-dimensional (bicyclic, tricyclic etc.). When the cavity of the macrocycle is spherical the molecule is called spherand. Other more exotic types are the calixarenes, cryptophanes, hemispherands and pondands.

Crown ethers are usually denoted by their total number of atoms and number of heteroatoms in the ring, plus substituents when present. Examples are 12-crown-4 (II), 15-crown-5 (III) and dicyclohexano-18-crown-6 (IV).

(II)

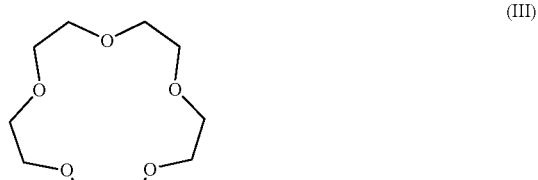

(III)

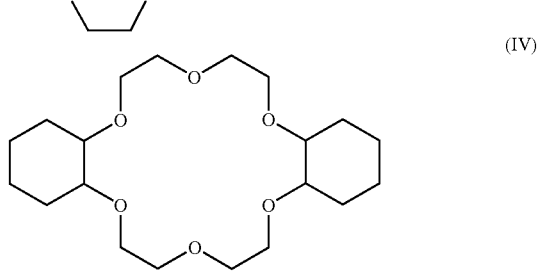

(IV)

In the present invention, the macrocyclic chelating compound is preferably selected from the group of crown ethers and cryptands. More preferably, the macrocyclic chelating compound is a crown ether. Even more preferably, the crown ether is 18-crown-6.

A macrocyclic chelating compound may be used in conjunction with any catalyst composition of the invention. However, a macrocyclic chelating compound is most usefully used when the halide is an alkali metal halide.

If a macrocyclic chelating compound is used in conjunction with a halide, the two compounds may be mixed to form a complex before addition to the reaction mixture or the macrocyclic chelating compound and the iodide may be added to the reaction mixture separately.

Suitably, the molar ratio of halide to macrocyclic chelating compound in the reaction mixture is at least 1:0.5, more suitably the molar ratio of halide to macrocyclic chelating compound is at least 1:0.75. Suitably, the molar ratio of halide to macrocyclic chelating compound is at most 1:10, more suitably the molar ratio of halide to macrocyclic chelating compound is at most 1:5.

The amount of water present is usually at least 0.2 mol/mol alkylene oxide present in the reaction mixture, preferably at least 0.5 mol/mol alkylene oxide. An amount of water present of at least 1 mol/mol alkylene oxide is most preferred. Preferably, the amount of water present is less than 25 mol/mol alkylene oxide, more preferably less than 15 mol/mol alkylene oxide. An amount of water present of at most 5 mol/mol alkylene oxide is most preferred.

A benefit of the present invention is that it is possible to carry out the process with high levels of activity and selectivity in the presence of a close to stoichiometric amount of water with respect to alkylene oxide, for example with an amount of water in the range of from 1 mol/mol alkylene oxide to 1.3 mol/mol alkylene oxide, especially with an amount of water of 1 mol/mol alkylene oxide or 1.1 mol/mol alkylene oxide. This reduces the amount of energy required for the removal of excess water from the reaction product.

The water present in the reaction mixture of the present invention may be added to the reaction mixture separately from the alkylene oxide. Alternatively the alkylene oxide and water may be pre-mixed before being supplied to the reactor. In a preferred embodiment of the invention, an alkylene oxide product mixture from an alkylene oxide reactor is used either without further process steps or after some concentration in a stripper. Most preferably, an ethylene oxide/water mixture, formed by absorption of the product stream from a direct oxidation ethylene oxide reactor is used. This method has a further benefit that the energy expended in isolating the alkylene oxide, prior to the process of the invention, is reduced.

Preferably, the total amount of carbon dioxide supplied to the reactor is in an amount of at least 0.5 mol/mol alkylene oxide, preferably at least 1 mol/mol alkylene oxide. Preferably the total amount of carbon dioxide supplied to the reactor is in an amount of at most 100 mol/mol alkylene oxide, more preferably an amount of at most 10 mol/mol alkylene oxide.

The process of the present invention may be carried out in batch operation. However, in particular for large-scale embodiments, it is preferred to operate the process continuously.

Suitable reaction temperatures for the catalytic preparation of alkylene glycols, according to the current invention are generally in the range of from 40 to 200° C., whereby temperatures in the range of from 50 to 120° C. are preferred.

The reaction pressure is usually selected in the range of from 100 to 5000 kPa, preferably in the range of from 200 to 3000 kPa, most preferably in the range of from 500 to 2000 kPa.

The following Examples will illustrate the invention. Examples 1 to 13 are of the invention and Examples 14 to 23 are comparative.

EXAMPLES

The Examples were carried out in either a 250 or a 125 ml Medimex autoclave according to the following procedures.

General Reaction Conditions

Examples 1 to 17 and 21 to 23

The reactor was filled with water and the halide (if present) was added in a sufficient quantity to provide a concentration of halide ions of 0.12 mol/l, the metalate or carbonate (if present) was added in a sufficient quantity to provide a concentration of 0.025 mol/l, and the crown ether (if present) was added in a sufficient quantity to provide a concentration of 0.19 mol/l. The reactor was then purged with $CO_2$ and pressurised with a $CO_2$ atmosphere of approximately 5 bar (500 kPa). The reactor content was then heated to the appropriate temperature (see Tables 1 and 2) and the reactor was further pressurised to 5, 10 or 20 bar (500, 1,000 or 2,000 kPa). The ethylene oxide was then pumped into the reactor at a rate of 6.3 g/min until a water/EO ratio of 4.02 mol/mol was reached. These conditions result in a halide concentration (if present) of 0.0118 mol/mol ethylene oxide and a metalate or carbonate concentration (if present) of 0.0035 mol/mol ethylene oxide. The reactor content was maintained at the appropriate temperature and pressure (by the continuous supply of $CO_2$) and samples were taken at regular time intervals and analysed by gas liquid chromatography (GLC).

Reaction Conditions

Examples 18 to 20

The reactor was filled with water and the halide catalyst (if present) was added in a sufficient quantity to provide a concentration of halide ions of 0.12 mol/l, the metalate catalyst was added in a sufficient quantity to provide a concentration of 0.025 mol/l and the crown ether (if present) was added in a sufficient quantity to provide a concentration of 0.19 mol/l. The reactor was then purged with $N_2$ and pressurised with an $N_2$ atmosphere of approximately 5 to 6 bar (500 to 600 kPa). The reactor content was then heated to 90° C. The ethylene oxide was then pumped into the reactor at a rate of 6.3 g/min (causing a pressure increase to approximately 10 to 14 bar (1000 to 1400 kPa)) until a water/EO ratio of 4.02 mol/mol was reached. These conditions result in a halide concentration (if present) of 0.0118 mol/mol ethylene oxide and a metalate concentration (if present) of 0.0035 mol/mol ethylene oxide. The reactor content was maintained at 90° C. and samples were taken at regular time intervals and analysed by GLC. During the course of the reaction, the pressure dropped back to the original 5 to 6 bar (500 to 600 kpa)(due to reaction of the ethylene oxide).

The results obtained are shown in Tables 1 and 2.

TABLE 1

| | | | | Examples of the Invention | | | | | |
| | | | | | | | | | |
| | | | Crown | | | Selectivity | | TOF[#] | Temperature | Pressure |
| | Iodide | Metalate | ether | Conversion* | EC | MEG | Total | ($h^{-1}$) | (° C.) | $CO_2$ (bar) |
| --- | --- | --- | --- | --- | --- | --- | --- | --- | --- | --- |
| 1 | KI | $K_2MoO_4$ | — | 97.6 | 0.4 | 96.7 | 97.1 | 57 | 90 | 20 |
| 2 | KI | $K_2MoO_4$ | 18-crown-6 | 100.0 | 2.5 | 96.6 | 99.1 | 62 | 90 | 20 |
| 3 | KI | $K_2MoO_4$ | 18-crown-6 | 99.5 | 2.2 | 96.6 | 98.8 | 74 | 90 | 20 |
| 4 | KI | $K_2WO_4$ | 18-crown-6 | 99.3 | 65.0 | 34.4 | 99.4 | 84 | 90 | 20 |
| 5 | KI | $Na_3VO_4$ | 18-crown-6 | 99.3 | 65.2 | 33.9 | 99.0 | 77 | 90 | 20 |

TABLE 1-continued

Examples of the Invention

|   | Iodide | Metalate | Crown ether | Conversion* | Selectivity EC | MEG | Total | TOF# $(h^{-1})$ | Temperature (°C.) | Pressure $CO_2$ (bar) |
|---|---|---|---|---|---|---|---|---|---|---|
| 6 | KI | $KVO_3$ | 18-crown-6 | 98.5 | 70.3 | 28.7 | 99.0 | 71 | 90 | 20 |
| 7 | TBPMI | $K_2MoO_4$ | — | 99.7 | 1.5 | 97.4 | 98.9 | 78 | 90 | 20 |
| 8 | TBPMI | $K_2MoO_4$ | 18-crown-6 | 99.7 | 4.4 | 94.8 | 99.2 | 84 | 90 | 20 |
| 9 | TBAI | $K_2MoO_4$ | — | 99.5 | 2.3 | 96.6 | 98.9 | 79 | 90 | 20 |
| 10 | TBAI | $K_2MoO_4$ | 18-crown-6 | 99.8 | 5.1 | 94.3 | 99.4 | 85 | 90 | 20 |
| 11 | KI | $K_2MoO_4$ | 18-crown-6 | 100.0 | 0.6 | 98.4 | 99.0 | 69 | 90 | 10 |
| 12 | KI | $K_2MoO_4$ | 18-crown-6 | 98.8 | 0.1 | 96.0 | 96.2 | 55 | 90 | 5 |
| 13 | TBPMI | $K_2MoO_4$ | — | 84.3 | 17.2 | 81.8 | 99.0 | 47 | 80 | 20 |

*conversion after 90 minutes;
TOF = Turn over frequency (moles of EC + moles of MEG produced/mole of iodide catalyst/h) calculated at 30 min;
TBPMI = tributylmethylphosphonium iodide;
TBAI = tetrabutylammonium iodide;
EC = ethylene carbonate.;
MEG = monoethylene glycol.

TABLE 2

Comparative Examples

|   | Iodide | Metalate/ carbonate | Crown ether | Conversion* | Selectivity EC | MEG | Total | TOF# $(h^{-1})$ | Temperature (°C.) | Pressure $CO_2$ (bar) |
|---|---|---|---|---|---|---|---|---|---|---|
| 14 | KI | — | 18-crown-6 | 99.2 | 84.6 | 15.0 | 99.6 | 75 | 90 | 20 |
| 15 | KI | $K_2CO_3$ | 18-crown-6 | 99.7 | 71.9 | 27.2 | 99.1 | 87 | 90 | 20 |
| 16 | — | $K_2MoO_4$ | — | 35.1 | 0.5 | 73.8 | 74.3 | — | 90 | 20 |
| 17 | — | $K_2MoO_4$ | 18-crown-6 | 32.4 | 0.4 | 75.4 | 75.8 | — | 90 | 20 |
| 18 | — | $K_2MoO_4$ | — | 46.2 | 0.0 | 78.0 | 78.0 | — | 90 | — |
| 19 | — | $K_2MoO_4$ | 18-crown-6 | 41.6 | 0.0 | 77.2 | 77.2 | — | 90 | — |
| 20 | KI | $K_2MoO_4$ | 18-crown-6 | 75.5 | 0.0 | 58.3 | 58.3 | 32 | 90 | — |
| 21 | TBPMI | — | — | 99.5 | 83.2 | 16.5 | 99.7 | 78 | 90 | 20 |
| 22 | TBPMI | — | — | 100.0 | 83.7 | 16.0 | 99.7 | 79 | 90 | 10 |
| 23 | TBPMI | $K_2CO_3$ | — | 100.0 | 83.9 | 15.8 | 99.7 | 91 | 90 | 20 |

*conversion after 90 minutes;
TOF = Turn over frequency (moles of EC + moles of MEG produced/mole of iodide catalyst/h) calculated at 30 min;
TBPMI = tributylmethylphosphonium iodide;
TBAI = tetrabutylammonium iodide;
EC = ethylene carbonate.;
MEG = monoethylene glycol.

The Examples of the invention demonstrate high levels of activity (as shown by the conversion results) and excellent selectivity to monoalkylene glycol.

The high total selectivity levels demonstrate low levels of formation of undesirable higher alkylene glycols even in the presence of a relatively small amount of water. Although Examples 4 to 6 (of the invention) demonstrate a reduced selectivity to monoethylene glycol (MEG) compared to the other Examples of the invention, these Examples all demonstrate a high total selectivity. Further, the selectivities to MEG for Examples 4 to 6 are higher than those of any of the comparative Examples in which a significant amount of the intermediate, ethylene carbonate, is formed (Examples 14, 15 and 21 to 23).

The Examples in Table 1, in comparison with the comparative Examples in Table 2, teach that the optimal results are obtained when $CO_2$ is present in combination with a catalyst composition comprising a halide carboxylation catalyst (optionally combined with a macrocyclic chelating compound) and an active metalate hydrolysis catalyst. An inferior performance is obtained if any of these three components ($CO_2$, halide, metalate) is absent.

In the absence of $CO_2$ (see comparative Examples 18 to 20), direct hydrolysis of the alkylene oxide to the alkylene glycol occurs, resulting in a significantly lower total selectivity (less than 78%), due to formation of undesired higher glycols.

In the absence of the halide carboxylation catalyst (see comparative Examples 16 to 19), very low activity (less than 46% conversion) and total selectivity levels are observed. Again, this is an indication that direct hydrolysis of the alkylene oxide to alkylene glycols is occurring, characterised by the significant formation of higher alkylene glycols. Example 16 is representative of the process described in JP-A-56,092, 228 and Example 19 is representative of the process described in EP-A-1,034,158.

In the absence of the metalate hydrolysis catalyst (see comparative Examples 14, 21 and 22) or in the presence of an alternative hydrolysis catalyst, such as $K_2CO_3$ (see comparative Examples 15 and 23), the major product is the alkylene carbonate. More severe reaction conditions would be needed to convert the alkylene carbonate into the desired alkylene glycol. Example 23 is representative of the process described in JP 2001151713 and JP 2001151711.

The invention claimed is:

1. A process for the conversion of an alkylene oxide to the corresponding alkylene glycol in the presence of a catalytic composition, carbon dioxide and water, wherein the catalytic composition comprises a halide, a metalate, and a macrocyclic chelating compound.

2. A process as claimed in claim 1, wherein the halide is an iodide selected from the group consisting of alkali metal iodides, quaternary phosphonium iodides and quaternary ammonium iodides.

3. A process as claimed in claim 1, wherein the metalate is selected from the group consisting of molybdates, vanadates and tungstates.

4. A process as claimed in claim 3, wherein the metalate is a molybdate.

5. A process as claimed in claim 1, wherein the macrocyclic chelating compound is a crown ether.

6. A process as claimed in claim 1, wherein the water is present in the range of from 0.2 to 25 mol/mol alkylene oxide present in the reaction mixture.

7. A process as claimed in claim 6, wherein the water is present in the range of from 1 to 5 mol/mol alkylene oxide present in the reaction mixture.

8. A process as claimed in claim 1, wherein the total amount of carbon dioxide supplied to the reactor is in an amount in the range of from 0.5 to 100 mol/mol alkylene oxide.

9. A process as claimed in claim 1, wherein the process takes place at a temperature in the range of from 40 to 200° C. and at a pressure in the range of from 100 to 5000 kPa.

10. A process as claimed in claim 1, wherein the alkylene oxide is ethylene oxide.

11. A process for the conversion of an alkylene oxide to the corresponding alkylene glycol in the presence of a catalytic composition, carbon dioxide and water, wherein the catalytic composition comprises a halide, a molybdate, and a macrocyclic chelating compound.

12. A process as claimed in claim 11, wherein the halide is an iodide selected from the group consisting of alkali metal iodides, quaternary phosphonium iodides and quaternary ammonium iodides.

13. A process as claimed in claim 11, wherein the macrocyclic chelating compound is a crown ether.

14. A process as claimed in claim 11, wherein the water is present in the range of from 1 to 5 mol/mol alkylene oxide present in the reaction mixture.

15. A process as claimed in claim 11, wherein the total amount of carbon dioxide supplied to the reactor is in an amount in the range of from 0.5 to 100 mol/mol alkylene oxide.

16. A process as claimed in claim 11, wherein the process takes place at a temperature in the range of from 40 to 200° C. and at a pressure in the range of from 100 to 5000 kPa.

17. A process as claimed in claim 11, wherein the alkylene oxide is ethylene oxide.

18. A process as claimed in claim 1, wherein the halide is a quaternary phosphonium iodide.

19. A process as claimed in claim 1, wherein the halide is a quaternary ammonium iodide.

20. A process as claimed in claim 11, wherein the halide is a quaternary phosphonium iodide.

21. A process as claimed in claim 11, wherein the halide is a quaternary ammonium iodide.

* * * * *